US009835593B2

(12) United States Patent
Kim

(10) Patent No.: US 9,835,593 B2
(45) Date of Patent: Dec. 5, 2017

(54) APPARATUS AND METHOD FOR DETERMINING CRACKED EGGS BY DRIVING VIBRATION

(71) Applicant: Jung Keun Kim, Daejeon (KR)

(72) Inventor: Jung Keun Kim, Daejeon (KR)

( * ) Notice: Subject to any disclaimer, the term of this patent is extended or adjusted under 35 U.S.C. 154(b) by 202 days.

(21) Appl. No.: 14/825,971

(22) Filed: Aug. 13, 2015

(65) Prior Publication Data

US 2017/0045479 A1    Feb. 16, 2017

(51) Int. Cl.
*G01N 29/24* (2006.01)
*G01N 29/44* (2006.01)
*G01N 29/12* (2006.01)

(52) U.S. Cl.
CPC ......... *G01N 29/12* (2013.01); *G01N 29/2412* (2013.01); *G01N 29/4436* (2013.01); *G01N 2291/014* (2013.01); *G01N 2291/0258* (2013.01); *G01N 2291/02466* (2013.01); *G01N 2291/101* (2013.01)

(58) Field of Classification Search
CPC ............... G01N 29/12; G01N 29/2412; G01N 29/4436; G01N 2291/014; G01N 2291/02466; G01N 2291/0258; G01N 2291/101
USPC .......................................................... 73/579
See application file for complete search history.

(56) References Cited

U.S. PATENT DOCUMENTS

| 5,696,325 | A | * | 12/1997 | Coucke | A01K 43/00 209/510 |
| 5,728,939 | A | * | 3/1998 | Moayeri | A01K 43/00 73/579 |
| 6,722,201 | B2 | * | 4/2004 | De Baerdemaeker | A01K 43/00 73/12.12 |
| 6,805,244 | B1 | * | 10/2004 | Toelken | A01K 45/00 119/6.8 |
| 9,194,769 | B1 | * | 11/2015 | Senibi | G06F 11/00 |
| 9,606,096 | B2 | * | 3/2017 | Van Wegen | G01N 33/08 |
| 9,625,362 | B2 | * | 4/2017 | Carbo | G01N 3/30 |

(Continued)

FOREIGN PATENT DOCUMENTS

JP    H08308098    11/1994

OTHER PUBLICATIONS

Food Reserach International, Relationship between dynamic resonance frequency and egg physical properties, Wang, et al., Sep. 9, 2003. Jiang.*

(Continued)

*Primary Examiner* — J M Saint Surin
(74) *Attorney, Agent, or Firm* — Stetina Brunda Garred & Brucker

(57) ABSTRACT

The present invention relates to an apparatus and a method for determining cracked eggs by driving vibrations without hitting eggs. The apparatus for determining cracked eggs comprises an integral type sensor and actuator which carries out applying a vibration to an egg in the state of contacting with the egg and detecting a vibration response signal corresponding to the vibration from the egg at the same time; a determination unit for determining whether or not the egg is cracked based on at least one of a resonance frequency and a quality factor of the vibration response signal detected from the integral type sensor and actuator; and a transport unit for moving the integral type sensor and actuator or the egg relatively to each other.

4 Claims, 7 Drawing Sheets

(56) References Cited

U.S. PATENT DOCUMENTS

2003/0127054 A1* 7/2003 Hebrank .............. A01K 45/007
                                                                                119/6.8
2015/0226654 A1* 8/2015 de Ketelaere .......... G01N 33/08
                                                                               702/43

OTHER PUBLICATIONS

Czech, Journal of Food Sciences, Eggshell Crack Detection Based on Acoustic Impulse Response and Supervised Patteern Recognition, Cai et al. Jan. 1, 2009.*

* cited by examiner

APPARATUS AND METHOD FOR DETERMINING CRACKED EGGS BY DRIVING VIBRATION

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates to an apparatus and a method for determining cracked eggs, more specifically, an apparatus and a method for determining cracked eggs by driving vibrations without striking eggs.

For a producer to produce eggs, the quality evaluation and grading process of eggs are important factors which determine the revenue of the producer. Therefore, it is highly necessitated to recognize the right value of high-quality eggs through the accurate selection. An egg includes multiple protective layers which protect the interior material, and the protective layers consist of a shell usually called an egg shell which surrounds the outermost portion, an outer membrane attached to the interior of the shell and an inner membrane surrounding albumen. When used in the specification herein, an egg shell membrane refers to the thing which includes the outer membrane and the inner membrane. A cracked egg is an egg that has a cracked shell but has the internal material not leaked because of an undamaged egg shell membrane, and it is very difficult to determine cracked eggs with the naked eye.

Currently, one conventional method for testing a cracked egg is the inspection with the naked eye by transmitting a light into an egg. This method has the possibility of erroneous determination due to the increased eye fatigue in the case of the exposure to light for a long time, and has difficulty in detecting a minute crack. In addition, the method does not guarantee the objectivity of quality because the determination is made by the inspector's subjectivity.

Another conventional method for detecting cracked eggs is Republic of Korea Patent No. 10-1139805, which was filed on Aug. 26, 2009 and has the title of the invention "Cracked Egg Quality Decision System and Method".

Referring to FIG. 1, the conventional striking type cracked egg detection system disclosed in Korea Patent No. 10-1139805 is shown. The system of Korea Patent No. 10-1139805 is configured to strike the equatorial portion or the buttocks of the egg several times using an impact bar while rotating an egg to be inspected, to accept the sound waves generated from the struck egg with a microphone, and to evaluate the quality of the egg, especially whether the egg is cracked or not, through the analysis of the sound wave signals.

These conventional striking type methods for determining cracked eggs have problems that (1) the accepted signal is inaccurate because an ambient noise as well as the desired sound wave signal are collected from the microphone and (2) the determination error is made by the delivery of the sound wave signal through surrounding microphones as well as an applicable microphone in the case of striking a plurality of eggs at the same time to sort out a plurality of eggs at the same time. In addition, (3) It is difficult to exactly determine cracked eggs because striking eggs with a constant force is difficult since the striking distance of an impact bar varies according to the size of the egg, and the strength of the signal varies according to the size of the egg. In addition, (4) in the case of providing multiple sorting devices in order to sorting out a plurality of eggs, the maintenance cost generated on the replacement of an impact bar or a microphone is increased because the device configuration is complicated by providing all impact bars and microphones in the narrow area.

BRIEF SUMMARY

The present invention has been made to solve the problems described above, and the object of the present invention is to provide an apparatus and a method for determining whether large amount of eggs are cracked or not at the same time. More specifically, the object of the present invention is to provide an apparatus and a method for determining whether eggs are cracked or not by applying vibrations and detecting the vibration response to the applied vibrations without striking the eggs using an impact bar.

A first embodiment of the present invention provides an apparatus for determining cracked eggs. The apparatus comprises an integral type sensor and actuator which carries out applying a vibration to an egg in the state of contacting with the egg and detecting a vibration response signal corresponding to the vibration from the egg at the same time; a determination unit for determining whether or not the egg is cracked based on at least one of a resonance frequency and a quality factor of the vibration response signal detected from the integral type sensor and actuator; and a transport unit for moving the integral type sensor and actuator or the egg relatively to each other.

In a second embodiment of the present invention, the integral type sensor and actuator comprises a magnetic material and a coil and is configured to apply a vibration to the egg by an electromagnetic force generated when a current flows in the coil and generate an electrical signal by the electromagnetic force caused by a vibration response corresponding to the vibration from the egg, or the integral type sensor and actuator comprises a piezoelectric element and is configured to apply a vibration to the egg by converting an electrical signal to the vibration of the piezoelectric element and generate an electrical signal from a vibration response of the egg corresponding to the applied vibration by the piezoelectric effect.

In a third embodiment of the present invention, the determination unit is configured to previously store a range of the resonance frequency and a reference value of a quality factor for vibration response signals of a normal egg and determine a target egg as a normal egg when the resonance frequencies of the target egg are within the range of the resonance frequency or quality factors of the target egg are larger than the reference value by analyzing the vibration response signals obtained in one or more of measuring positions of a surface of the target egg by the vibration response detecting unit.

The other embodiment of the present invention provides a method for determining cracked eggs. The method comprises steps of applying a vibration to an egg in a state of contacting with the egg by an integral type sensor and actuator; detecting a vibration response signal corresponding to the vibration applied by applying the vibration from the egg by the integral type sensor and actuator; moving the integral type sensor and actuator or the egg relatively to each other; and a step of determining whether or not the egg is cracked based on at least one of a resonance frequency and a quality factor of the vibration response signal detected in the detecting, by a determination unit.

According to the first embodiment, since a contact type detector is used without striking eggs using an impact bar, the determination result of cracked eggs is not affected by an ambient noise and whether or not the eggs are cracked is determined by the vibration response of the surface of the eggs, which may reduce determination errors by the ambient noise. Accordingly, when determining large amount of eggs, it is possible to measure each of a plurality of eggs at the same time without interference by measurement conditions in other eggs. It is very effective compared to conventional striking type determination method because it is possible to overcome the problem that the conventional striking type determination method for cracked eggs generates determination errors by the delivery of sound wave signals through surrounding microphones as well as an applicable microphone by the striking noise and because it is possible to determine whether or not a plurality of eggs are cracked at the same time by providing a plurality of determination devices within a single system.

Further, the determination result is not affected by the size of the egg since whether the egg is cracked or not is determined in the state of making a contact with the egg.

Further, since the vibration driving unit and the vibration response detecting unit are implemented as an integrated module and the integrated module is configured to apply vibration to the egg by converting the electrical signal into the vibration while detecting the vibration response signal corresponding to the vibration from the egg, the integrated module has an additional effect of being able to determine cracked eggs with a simple configuration and at a low cost.

According to the third embodiment, it is possible to determine cracked eggs with ease by predetermined criteria.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Hereinafter, embodiments of the present invention will be described in detail with reference to the accompanying drawings. Besides, in the following description of the present invention, a detailed description of related known configurations or functions will be omitted if the detailed description thereof is considered to obscure the gist of the present invention.

Figure 1:
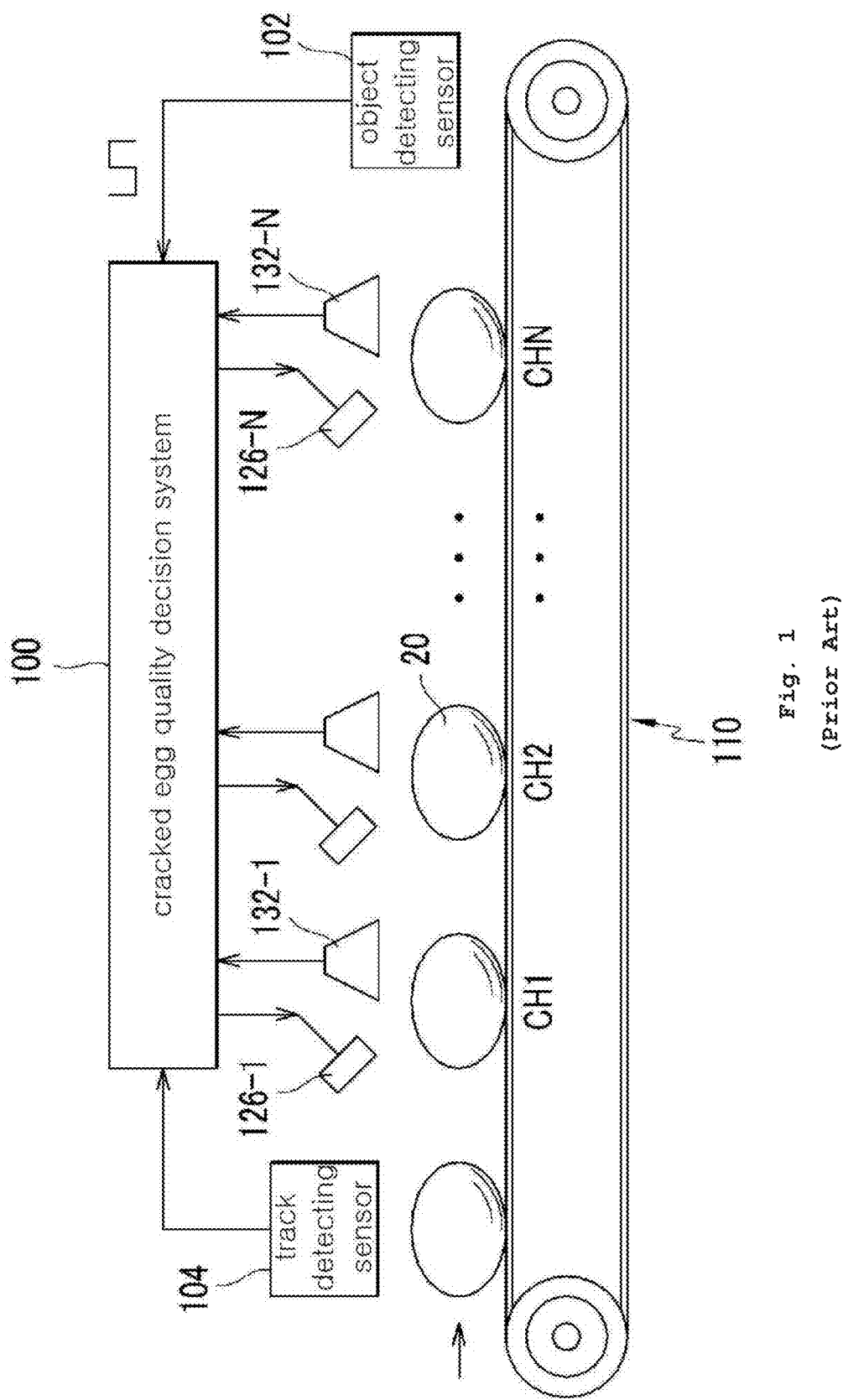
FIG. 1 shows a conventional striking type cracked egg determination system.
Figure 2:
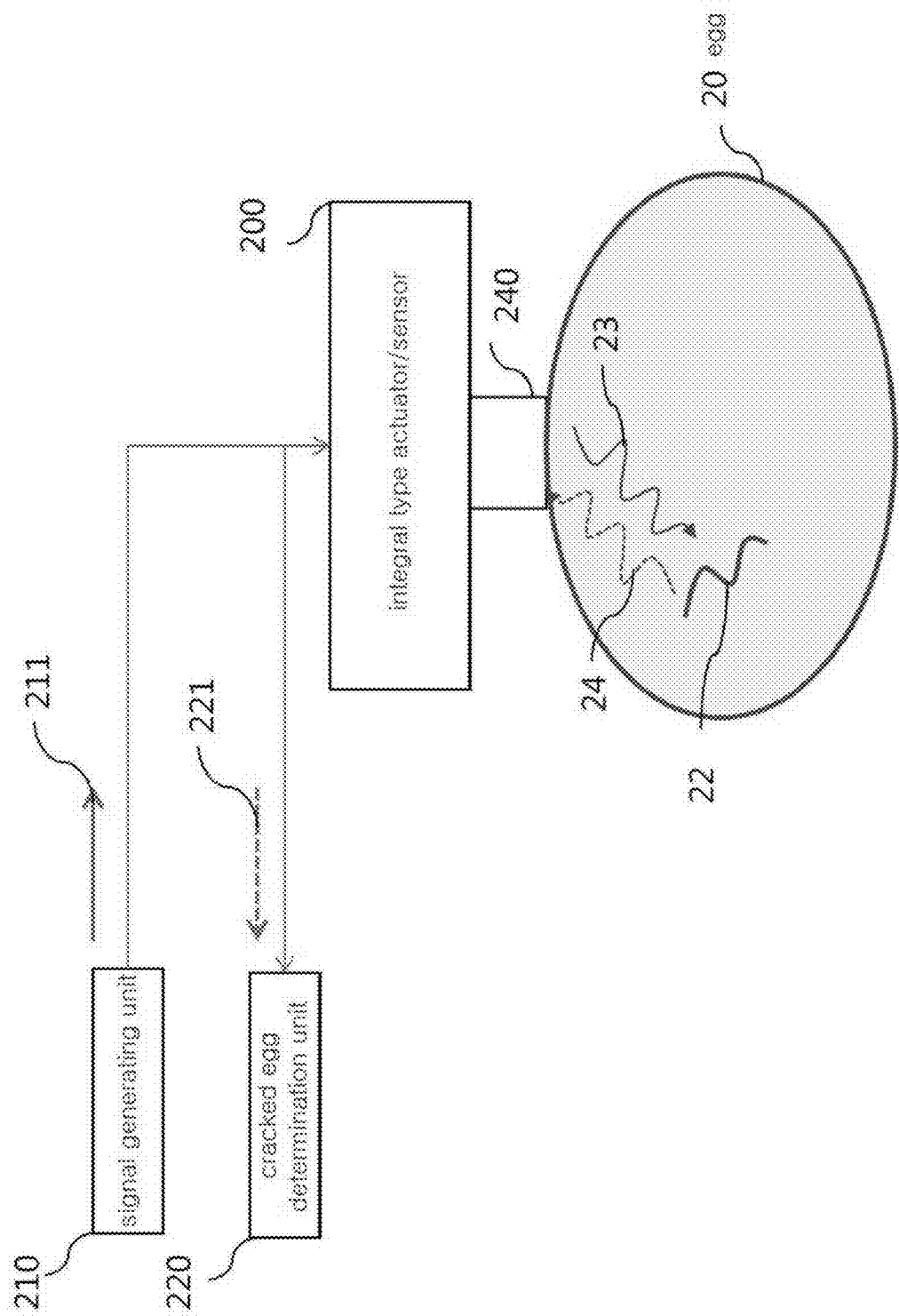
FIG. 2 shows a schematic diagram of an apparatus for determining a cracked egg of the present invention.

Referring to FIG. 2, there is shown a schematic diagram of an apparatus for determining cracked eggs of the present invention. In an embodiment of the present invention, a vibration driving unit for applying a vibration to an egg and a vibration response detecting unit for detecting a vibration response signal corresponding to the vibration applied by the vibration driving unit from the egg may consist of a single module. This module is shown as an integral type actuator/sensor 200 in FIG. 2. In the specification of the present invention, the integral type actuator/sensor is interchangeably used with an integral type sensor and actuator.

The present invention is configured to contact a measurement probe 240 attached to a lower portion of the integral type actuator/sensor 200 with a surface of a egg 20 by constant force, as shown in FIG. 2. In the present embodiment, it has been described to apply a vibration to the surface of the egg 20 through the measurement probe 240. However, without being limited to this, it is possible to design the integral type actuator/sensor 200 to apply a vibration in direct contact with the surface of the egg 20.

A signal generating unit 210 may transmit an actuator excitation signal 211 to the integral type actuator/sensor 200 by generating various frequency components one by one in sequence, or may transmit an actuator excitation signal 211 to the integral type actuator/sensor 200 by generating various frequency signals at the same time and combining the generated signals. This excitation signal 211 generates egg surface excitation 23 on the egg 20 through the probe 240. After applying vibrations to the egg, an egg surface response 24 corresponding to the vibrations is transmitted sequentially passing through the probe 240 and the integral type actuator/sensor 200. A cracked egg determination unit 220 determines whether an egg is cracked or not by observing the changes in voltage corresponding to the vibration response signals. Those having ordinary skill in the art would understand that an analog-to-digital converter ADC converting an egg surface response measurement signal 221 to a digital signal and a digital signal processor DSP configured to analyze the characteristics of the frequency such as amplitude and phase of the vibration response signal may be included in the cracked egg determination unit 220 or may be provided between the integral type actuator/sensor 200 and the cracked egg determination unit 220.

When applying vibrations to the egg, the egg surface response 24 exhibits the maximum vibration at natural frequency of the egg itself, that is, at a resonance frequency. If the egg is normal, the vibration characteristic having a high value in a narrow frequency band appears on the egg surface response 24. If the egg is cracked, however, the overall low frequency characteristic in a wide frequency band appears on the egg surface response 24.

Although not shown in FIG. 2, after the measurement of the egg 20 is completed, a cracked egg determining system of the present invention may further comprise a transport unit for moving the integral type actuator/sensor 200 or the egg 20 relatively to each other.

Figure 3:
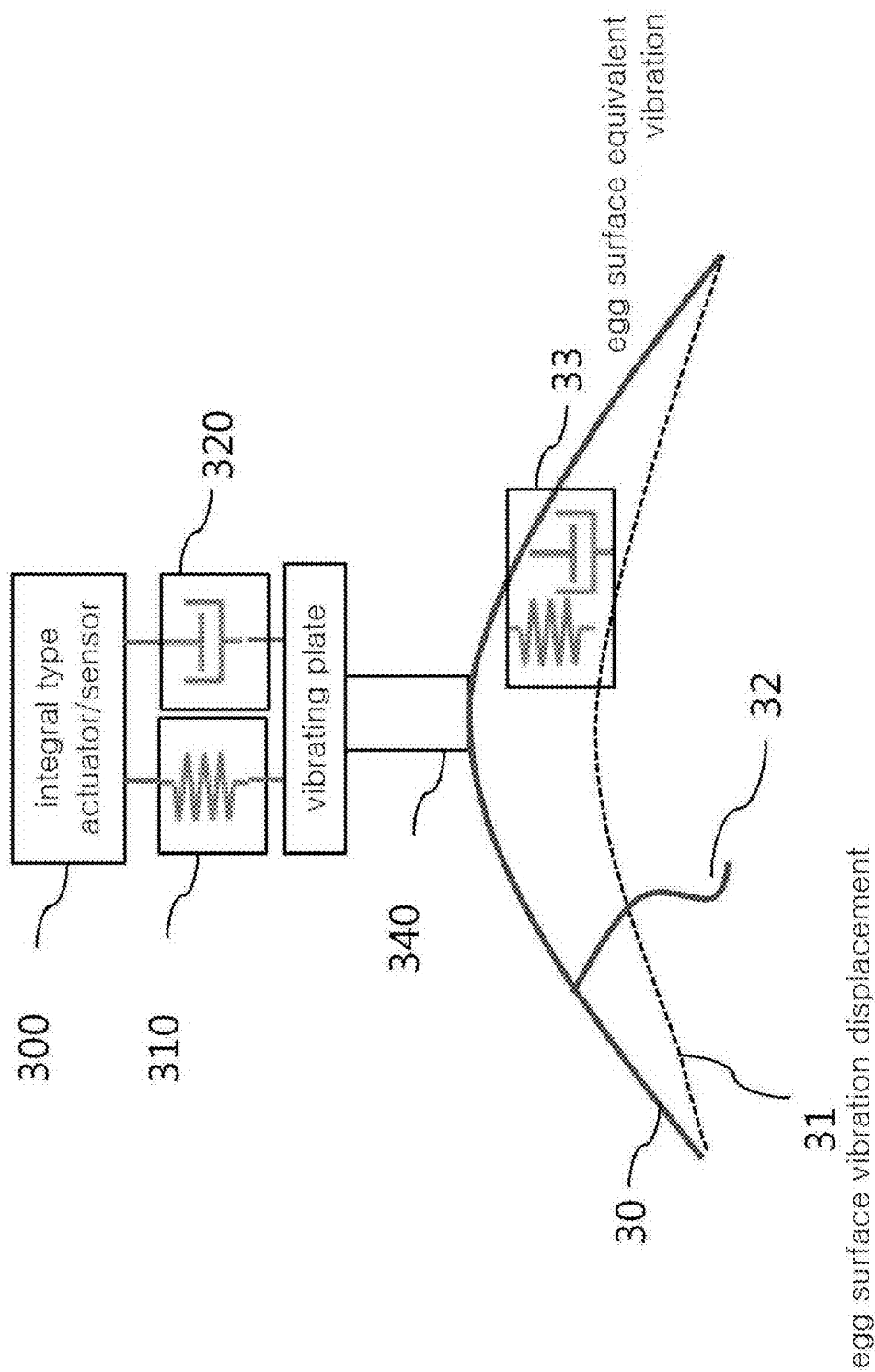
FIG. 3 shows a schematic diagram modeling vibrations in the integral type actuator/sensor or an egg of the present invention.

Now, referring to FIG. 3, a schematic diagram modeling the integral type actuator/sensor of the present invention or the vibration in the egg is shown. The vibration characteristic described with reference to FIG. 2 is described in more detail through FIG. 3. The vibration by an integral type actuator/sensor 300 may be modeled as a mass-spring-damper structure, which is represented by reference numerals 310 and 320 in FIG. 3. An equivalent vibration on the surface of an egg 30 is represented by a reference numeral 33. A vibration which is applied in a detector provided with the integral type actuator/sensor 300 makes the integral type actuator/sensor 300, probe 340 and the surface of the egg 30 vibrate. Further, in the case of an egg, it has a different vibration characteristic according to whether it has cracked portion 32 or it is normal.

The integral type actuator/sensor of the present invention is configured to apply the vibration to the egg by converting an electrical signal to the vibration while detecting the vibration response signal corresponding to the vibration from the egg. That is, the integral type actuator/sensor is produced with a structure in which electrical signals and vibration signals may be mutually converted so that vibration variation of the actuator can take place by electrical signals and electrical signals can change according to vibration variation of the actuator.

An example of the integral type actuator/sensor for achieving above structure may be configured with a magnetic material such as a permanent magnet and with a coil in which a current flows. Vibrations may be generated on the contact type probe by using an electromagnetic force generated when the current flows in the coil. The vibration of the probe applies the vibration to an egg. In addition, the electrical signal is generated by the electromagnetic force when the contact type probe vibrates by the vibration generated in the egg, so it is possible to accept the vibration signal of the egg using this signal. Another example of the integral type actuator/sensor may be a piezoelectric element. Measuring the vibration signal of an egg using a piezoelectric element includes applying the vibration to the egg by converting the electrical signal into the vibration of the piezoelectric element, and converting the vibration of the egg into the electrical signal using a piezoelectric effect.

However, the integral type actuator/sensor of the present invention is not limited to the above examples. Those skilled in the art would appreciate that it may include any means being capable of determining cracked eggs using the principle of applying the vibration to the egg through converting the electrical signal into the vibration signal and of measuring the vibration of the egg that is converted into the electrical signal.

Figure 4:
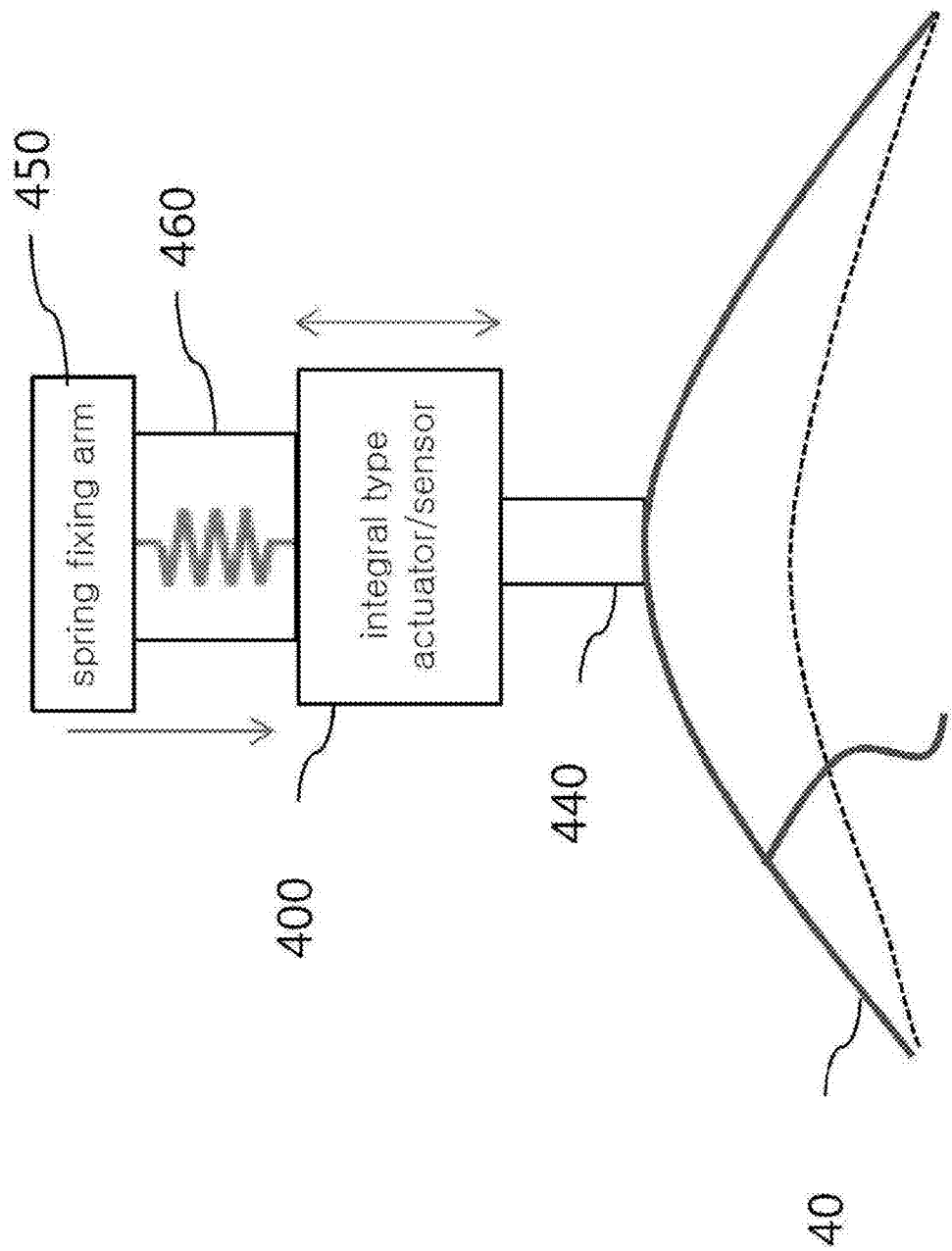
FIG. 4 shows a configuration example of an embodiment of the present invention for maintaining a constant contact force between an integral type actuator/sensor and an egg.

Now, referring to FIG. 4, an embodiment of the present invention is shown provided with a contact control spring 460 and a spring fixing arm 450 in an upper surface of an integral type actuator/sensor 400 to maintain a constant contact force between the integral type actuator/sensor and an egg.

As shown in FIG. 4, when the contact control spring 460 is provided in the upper surface of the integral type actuator/sensor 400, the contact force between the egg and the integral type actuator/sensor 400 or between the egg and a probe 440 may be constant. As an alternative to make the contact force constant, in addition to the method of using springs 460, the spring fixing arm 450 or the self-weight of the integral type actuator/sensor 400 may be used. It is also possible to use a combination of two or more of the methods.

However, those skilled in the art would appreciate that the means for a constant contact force of the present invention is not limited to the above examples but may comprise any means for a constant contact force between an egg and an integral type actuator/sensor.

In order to contact an egg 40 with the integral type actuator/sensor 400, it is possible to fix the egg and transfer the integral type actuator/sensor 400 in the direction of the egg until a constant contact force arises. It is also possible to fix the integral type actuator/sensor 400 and transfer the egg 40 in the direction of the integral type actuator/sensor 400 to have a constant contact force.

In the present invention described above, since a contact type detector is used without striking an egg using an impact bar, the determination result of a cracked egg is not affected by ambient noise and whether or not the eggs are cracked is determined by the vibration response of the surface of the eggs. Thus, determination errors by ambient noise may be reduced. Accordingly, when determining a large amount of eggs, it is possible to measure each of a plurality of eggs at the same time without interference by measurement conditions in other eggs. It is very effective compared to conventional striking type determination method because it is possible to overcome the problem of the conventional striking type cracked egg determination method which causes determination errors by the delivery of sound wave signals through surrounding microphones as well as an applicable microphone by the striking noise and because it is possible to determine whether or not a plurality of eggs are cracked at the same time by providing a plurality of determination devices within a single system. In addition, since the actuator and the sensor are configured as a single module, it is possible to apply vibration to eggs by converting the electrical signal into the vibration while detecting the vibration response signal corresponding to the vibration from the eggs. Thus, there is an additional effect of being able to determine cracked eggs with a simple configuration and at a low cost.

Figure 5:
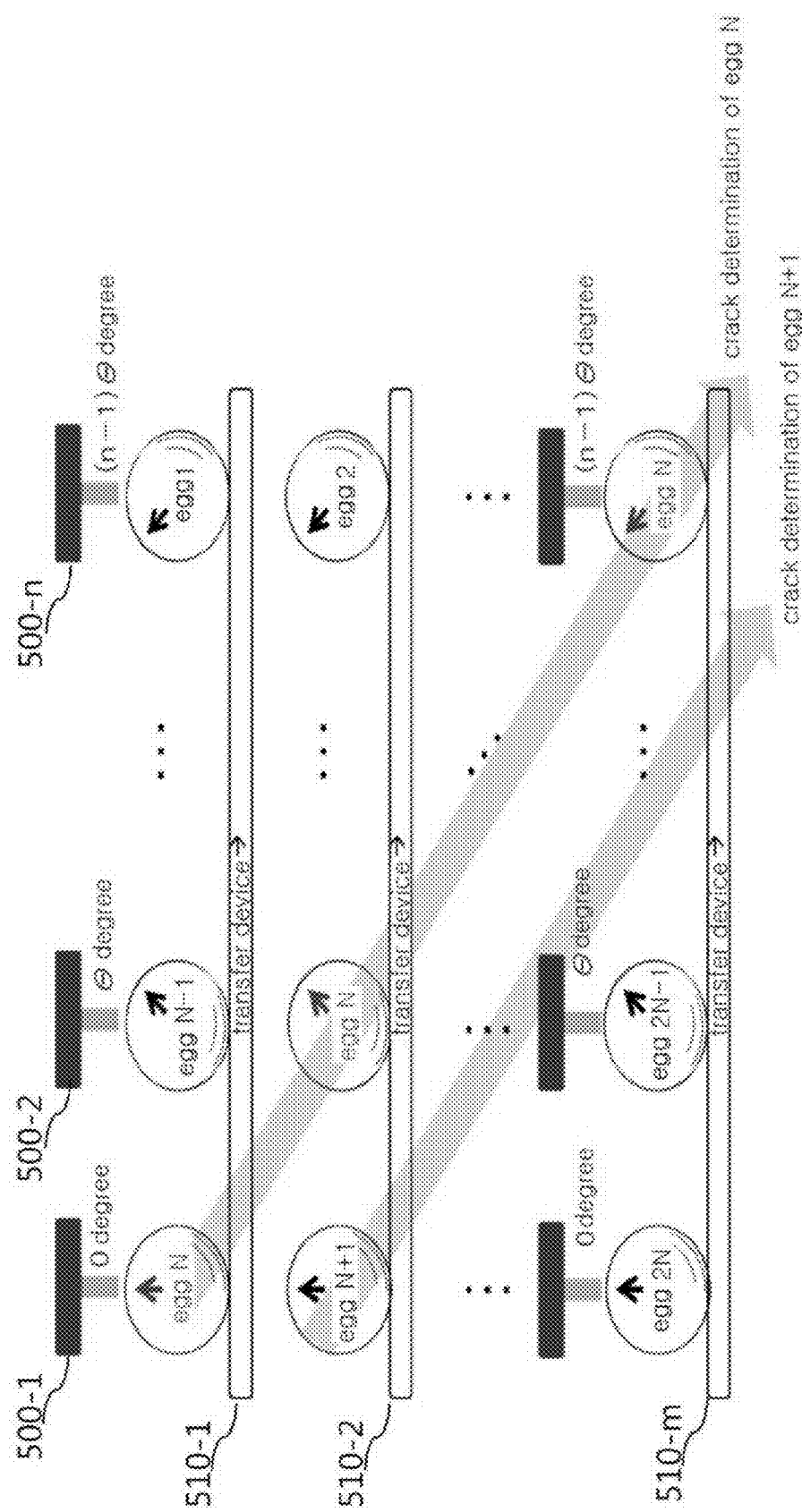
FIG. 5 shows a system which is capable of simultaneously determining whether a plurality of eggs is cracked or not by providing a plurality of determination apparatuses according to the present invention within a single system.

FIG. 5 shows a system that may determine whether or not a plurality of eggs is cracked at the same time by providing a plurality of determination devices within a single system in order to maximize the aforementioned effect.

As shown in FIG. 5, a plurality of integral type actuators/sensors 500-1 to 500-$n$ and a plurality of egg transfer devices 510-1 to 510-$m$ are provided in order to determine whether or not several eggs are cracked. The terms 'transfer device' and 'transfer unit' in the present specification are used interchangeably. The egg transfer devices 510-1 to 510-$m$ transfer eggs from one of the actuators/sensors to the next actuators/sensors, while rotating the eggs. From the point of view of one transfer device, after whether or not an egg is cracked is determined primarily in a first integral type actuator/sensor 500-1, the transfer device rotates the egg, thereby the egg is rotated and located in the lower portion of a second integral type actuator/sensor 500-2 and whether or not the egg is cracked is determined secondarily. By a plurality of times of the rotation and determination, whether or not the egg is cracked may be determined in various spots of the egg. Unlike the above method, it is also possible to determine whether or not an egg is cracked while fixing the egg and moving the integral type actuator/sensor with respect to the egg.

When "m" number of such a transfer device is provided in the horizontal direction, whether or not a plurality of eggs is cracked may be determined at the same time. When "n*m" number of the integral type actuator/sensor is provided, whether or not "m" number of the egg is cracked may be determined at a time. In the present method, since there is no interference with the signals measuring adjacent eggs by using the contact type detector unlike the striking type determination method which causes striking noise, it is possible to configure a high-speed determination system through performing simultaneous measurement.

In one egg, if all the frequency analysis signals in the set positions are obtained, it becomes easy to determine whether the egg is normal or cracked through the correlation between a maximum resonance frequency and a Q value (quality factor). Naturally, if the eggs from a farm are assumed to have a constant size and similar quality, it is possible to use the correlation between maximum resonance frequencies and Q values of other eggs for more reliable determination of a target egg.

Figure 6:
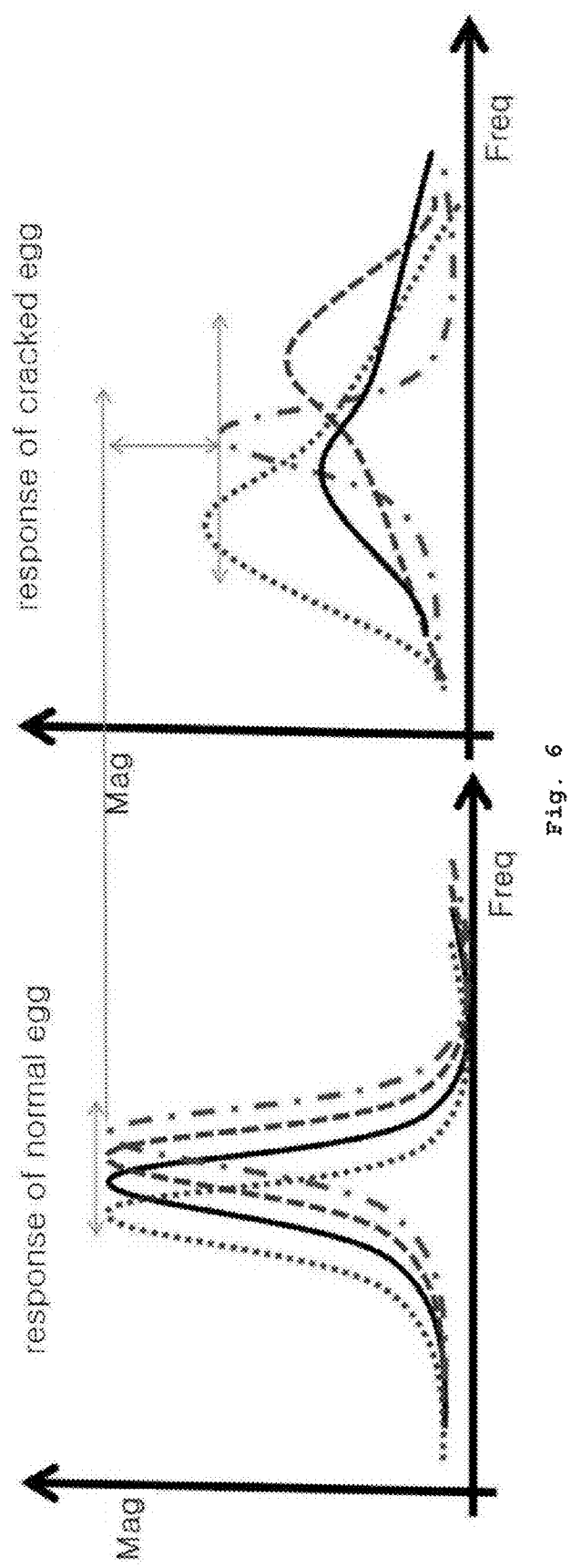
FIG. 6 shows frequency characteristics of a normal egg and a cracked egg obtained through a contact type detector of the present invention.

FIG. 6 shows frequency characteristics of a normal egg and a cracked egg obtained through the contact type detector. When the detecting position of an egg rotates and changes, the normal egg shows a high Q value and its frequency response curve shows the frequency response curve with the form which seems to shift to the x-axis direction although the center frequency is slightly changed according to the rotational position. On the other hand, in the case of cracked eggs, even a single frequency response shows a low Q value and the variation of center frequencies is slightly larger than that of normal eggs. Thus, when looking at the correlation between frequency responses at each position, the correlation index of the normal egg appears very high and the correlation index of the cracked egg appears low; these correlations are indicator for determining the cracked egg.

The frequency characteristic may be used to determine a cracked egg as follows: a range of a resonance frequency and a reference Q value for vibration response signals of a normal egg is previously stored, and then, the vibration response signals obtained in one or more of measuring positions of the surface of an egg are analyzed. If the resonance frequencies of the vibration response signals are within the range of the resonance frequency or the Q values are larger than the reference Q value, the egg under examination is determined as a normal egg.

For reference, a Q value means a Quality factor that represents an attenuation rate in the vibration signal. If a Q value is large, it means that the frequency bandwidth is narrow and the attenuation is low. If a Q value is small, it means that the frequency bandwidth is wide and the attenuation is high. In the case of a cracked egg, the attenuation and non-uniformity of vibration characteristic caused by a cracked portion is shown, through which it is possible to determine a crack.

A method for determining a cracked egg of the present invention comprises steps of: applying a vibration to an egg in the state of contacting with the egg by a vibration driving unit (or an integral type actuator/sensor); detecting a vibration response signal corresponding to the vibration applied by applying the vibration from the egg by the vibration response detecting unit (or the integral type actuator/sensor); moving the vibration driving unit and the vibration response detecting unit (or the integral type actuator/sensor) or the eggs relatively to each other; and determining whether or not the egg is cracked based on at least one of the resonance frequency and the Q value (Quality factor) of the vibration response signal detected in the detecting, by a determination unit.

Figure 7:
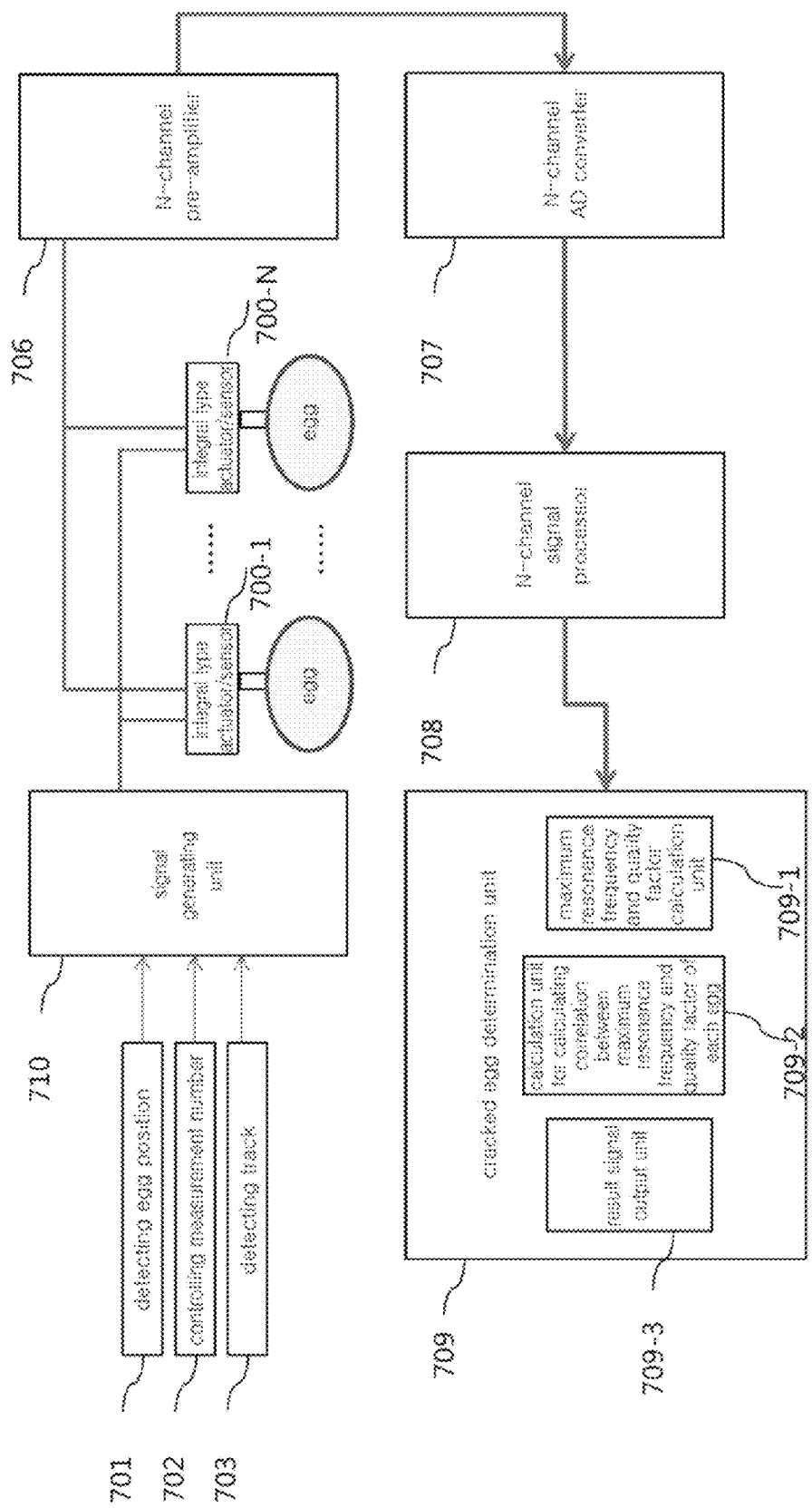
FIG. 7 shows an overall structure of a cracked egg detecting system according to the present invention.

FIG. 7 shows an overall structure of a cracked egg detecting system. An egg position detecting sensor 701 is configured to detect the position of an egg, a measurement numbering controller 702 is configured to calculate the number of measurements, and a track sensor 703 is configured to detect a track in which the egg is rotated. When a target egg is transferred to an inspection location using transfer means and the target egg has reached the inspection location, one or more of integral type actuators/sensors 700-1 to 700-N are moved to make contact with the surface of the target egg. A signal generating unit 710 is configured to apply vibrations through the integral type actuators/sensors 700 by generating excitation signals. The signals obtained from the vibration responses of the egg in a plurality of locations through the integral type actuators/sensors 700 are amplified through an N-channel pre-amplifier 706. An N-channel AD converter 707 is configured to convert an amplified analog signal to a digital signal. An N-channel signal processor 708 is configured to process the converted digital signal appropriately before analyzing the frequency. For example, the signal processing may be a filtering for removing noise from the digital signal. A cracked egg determination unit 709 may include a maximum resonance frequency and Q value calculation unit 709-1, a calculation unit for calculating the correlation between the maximum resonance frequency and the Q value of each egg 709-2, and a result signal output unit 709-3. Although not described in detail in FIG. 7, contact type detectors and egg transfer devices are extensible in a two-dimensional array as well as a one-dimensional array, and it is possible for the contact type detectors and egg transfer devices to be configured in the form of constantly modularizing depending on the calculating ability of the determination unit and extending the module.

Although the above are described features and effects of various embodiments of the present invention with detailed descriptions about structures and functions of various embodiments of the present invention, the detailed description is for illustrative purposes only. Thus, changes may be made to the maximum range indicated by extended general sense which is described in the appended claims, and the scope of the present invention is determined by the claims.

What is claimed is:

1. An apparatus for determining a cracked egg, comprising:
    an integral type sensor and actuator which carries out applying a vibration to an egg in the state of contacting with the egg and detecting a vibration response signal corresponding to the vibration from the egg at the same time;
    a determination unit for determining whether or not the egg is cracked based on at least one of a resonance frequency and a quality factor of the vibration response signal detected from the integral type sensor and actuator; and
    a transport unit for moving the integral type sensor and actuator or the egg relatively to each other; and
    wherein the determination unit is configured to previously store a range of the resonance frequency and a reference value of a quality factor for vibration response signals of a normal egg and determine a target egg as a normal egg when the resonance frequencies of the target egg are within the range of the resonance frequency or quality factors of the target egg are larger than the reference value by analyzing the vibration response signals obtained in one or more of measuring positions of a surface of the target egg by the vibration response detecting unit.

2. The apparatus of claim 1, wherein the integral type sensor and actuator comprises a magnetic material and a coil, the integral type sensor and actuator being configured to apply a vibration to the egg by an electromagnetic force generated when a current flows in the coil and generate an electrical signal by the electromagnetic force caused by a vibration response corresponding to the vibration from the egg, or
    the integral type sensor and actuator comprises a piezoelectric element, the integral type sensor and actuator being configured to apply a vibration to the egg by converting an electrical signal to the vibration of the piezoelectric element and generate an electrical signal, from, a vibration response of the egg corresponding to the applied vibration by the piezoelectric effect.

3. A method for determining a cracked egg, comprising steps of:

applying a vibration to an egg in a state of contacting with the egg by an integral type sensor and actuator;

detecting a vibration response signal corresponding to the vibration applied by applying the vibration from the egg by the integral type sensor and actuator;

moving the integral type sensor and actuator or the egg relatively to each other; and determining whether or not the egg is cracked based on at least one of a resonance frequency and a quality factor of the vibration response signal detected in the detecting, by a determination unit; and wherein the determining step further comprises previously storing a range of the resonance frequency and a reference value of a quality factor for the vibration response signals of a normal egg and determining a target egg as a normal egg when the resonance frequencies of the target egg are within the range of the resonance frequency or quality factors of the target egg are larger than the reference value by analyzing the vibration response signals obtained in one or more of measuring positions of a surface of the target egg in the detecting the vibration response signal.

4. The method of claim 3, wherein the integral type sensor and actuator comprises a magnetic material and a coil, the integral type sensor and actuator being configured to apply a vibration to the egg by an electromagnetic force generated when a current flows in the coil and generate an electrical signal by the electromagnetic force caused by a vibration response corresponding to the vibration from the egg, or the integral type sensor and actuator comprises a piezoelectric element, the integral type sensor and actuator being configured to apply a vibration to the egg by converting an electrical signal to the vibration of the piezoelectric element and generate an electrical signal from a vibration response of the egg corresponding to the applied vibration by the piezoelectric effect.

* * * * *